United States Patent [19]

Kojima et al.

[11] Patent Number: 4,863,584

[45] Date of Patent: Sep. 5, 1989

[54] APPARATUS FOR SENSING AIR-FUEL RATIO

[75] Inventors: Takao Kojima; Hiroyuki Ishiguro; Yoshihide Kami, all of Nagoya, Japan

[73] Assignee: NGK Spark Plug Co., Ltd., Aichi, Japan

[21] Appl. No.: 190,144

[22] Filed: May 4, 1988

[30] Foreign Application Priority Data

May 12, 1987 [JP] Japan .................. 62-115531

[51] Int. Cl.$^4$ ............................. G01N 27/46
[52] U.S. Cl. ................... 204/425; 204/412; 204/426
[58] Field of Search ............... 204/15, 421–429

[56] References Cited

U.S. PATENT DOCUMENTS

| | | | |
|---|---|---|---|
| 4,207,159 | 6/1980 | Kimura et al. | 204/426 |
| 4,282,080 | 8/1981 | Muller et al. | 204/428 |
| 4,498,968 | 2/1985 | Yamada et al. | 204/426 |
| 4,574,627 | 3/1986 | Sakurai et al. | 204/426 |
| 4,578,171 | 3/1986 | Yamada et al. | 204/412 |
| 4,578,172 | 3/1986 | Yamada et al. | 204/425 |
| 4,579,643 | 4/1986 | Mase et al. | 204/428 |
| 4,639,305 | 1/1987 | Shibata et al. | 204/426 |
| 4,645,572 | 2/1987 | Nishizawa et al. | 204/425 |
| 4,765,880 | 8/1988 | Hayakawa et al. | 204/426 |
| 4,769,124 | 9/1988 | Okada et al. | 204/426 |

FOREIGN PATENT DOCUMENTS 59-178354 10/1984 Japan .
60-129656 7/1985 Japan .
60-131452 7/1985 Japan .
60-192250 9/1985 Japan .
61-251766 11/1986 Japan .

Primary Examiner—T. Tung
Attorney, Agent, or Firm—Oliff & Berridge

[57] ABSTRACT

An apparatus for sensing air-fuel ratio of the present invention is capable of measuring an air-fuel ratio of the air-fuel combustion mixture by sensing a partial pressure of oxygen in the exhaust gas. This apparatus forms a gas regulation chamber by arranging oxygen ion conductive solid electrolytes opposite to each other through a gap. In the gas regulation chamber, diffusion of exhaust gas is regulated. Porous electrodes are formed on both sides of the solid electrolytes. One sensor element formed by one of the solid electrolytes is operated as an oxygen concentration cell element, while the other sensor element formed by the other solid electrolyte is operated as an oxygen pump element. Moreover, the sensor elements are heated in order to activate such elements by heaters provided separately. A constant current is supplied to the oxygen concentration cell element in such a direction as pumping the oxygen into the gas regulation chamber. Supply of a constant current to the oxygen concentration cell element allows existence of a fixed output voltage from the oxygen concentration cell element even when the heater voltage changes. Accordingly, an air-fuel ration can be sensed accurately, independent of change in heater voltage which has been considered as a cause of problem, by controlling a supply current to the oxygen pump element so that an output voltage of the oxygen concentration cell element becomes the fixed voltage and then sensing the air-fuel ratio from such current value.

6 Claims, 6 Drawing Sheets

APPARATUS FOR SENSING AIR-FUEL RATIO

BACKGROUND OF THE INVENTION

1. Technical Field

The present invention relates to an apparatus for sensing air-fuel ratio which senses air-fuel ratio of air-fuel mixture gases supplied to a combustion apparatus on the basis of oxygen content in the exhaust gas of a variety of combustion apparatuses, e.g., an internal combustion engine.

2. Prior Art

For instance, the Published Unexamined Japanese Patent Application No. 59-178354 discloses a typical air-fuel ratio sensor which senses air-fuel ratio of air-fuel mixture gases supplied on a combustion apparatus such as internal combustion engine by detecting the oxygen content in the exhaust gas. In this case, a porous electrode is formed to both sides of the oxygen ion conductive solid electrolyte in order to complete a sensor element, a pair of such sensor elements are arranged opposite to each other with a gap therebetween. The gap forms a gas-diffusion regulation chamber in which diffusion of exhaust gas is limited.

This air-fuel ratio sensor operates one sensor element as an oxygen concentration cell element, and the other sensor element as an oxygen pump element. The ar-fuel ratio sensor of this type provides, on one hand, a measuring circuit which controls a current flowing into the oxygen pump element so that a voltage generated at the electrodes of the oxygen concentration cell element becomes constant. The air-fuel ratio is determined from such a current value. On the other hand, another type of oxygen sensor provides a measuring circuit which makes a constant current flow into the oxygen pump element in such a direction as pumping the oxygen in the gas-diffusion regulation chamber to the circumference thereof. The air-fuel ratio, is determined from a voltage generated at the electrodes of the oxygen concentration cell element.

The oxygen ion conductive solid electrolyte which forms the sensor element increases mobility of oxygen ion with increase in temperature, and a mobility of the oxygen sufficient for normal operation of the oxygen concentration cell element or oxygen pump element is achieved at the temperature higher than a certain value. On the other hand, a voltage generated at the electrodes on both sides of the oxygen concentration cell element or a current flowing into the oxygen pump element changes in accordance with change in ambient temperature. Therefore, the air-fuel ratio sensor is usually provided with a heater formed by a heat-generating resistor, etc., for the purpose of activation of the sensor element and temperature compensation, and heats the sensor element by applying a voltage to the heater from the measuring circuit.

Therefore, an apparatus for sensing air-fuel ratio which is provided with the air-fuel ratio the sensor is capable of easing the effect of temperature change of sensor element by the heater even in case of ambient temperature changes and thereby stably senses the air-fuel ratio. However, this apparatus provides a problem, when heat-generated by the heater changes due to fluctuation of voltage applied to the heater, that the air-fuel ratio cannot be sensed stably because of resultant change in the temperature of the sensor element. Accordingly, the prior art is required to accurately control a voltage applied to the heater and thereby results in a problem that a special electrical circuit for controlling the heater voltage must be provided additionally.

SUMMARY OF THE INVENTION

Therefore, an object of the present invention is to provide an apparatus for sensing air-fuel ratio which can sense air-fuel ratio with excellent accuracy, even if a voltage to be applied to the heater changes and even if atmospheric pressure changes.

Namely, the present invention proposed to attain the object explained above provides an apparatus for sensing air-fuel ratio comprising:

an air-fuel ratio sensor for sensing oxygen concentration in an exhaust gas, said air-fuel ratio sensor including two sensor elements each of which is formed by coating a pair of porous electrodes on both surfaces of an oxygen ion conductive solid electrolyte plate, a gas-diffusion regulation chamber which faces either surface of the porous electrode and restricts diffusion of the exhaust gas, and a heater which heats said two sensor elements, voltage-applying means for applying voltage to said heater in order to heat said two sensor elements, means for outputting an air-fuel ratio signal responsive to the oxygen concentration in the exhaust gas by making one of said two sensor elements operate as an oxygen concentration cell element and the other operate as an oxygen pump element and outputs air-fuel ratio signal according to oxygen concentration in the exhaust gas, and current-supply means for supplying electric current to said oxygen concentration cell element by applying preset voltage to said oxygen concentration cell element, current having such a direction as to transport oxygen gas from ambient exhaust gas to said gas diffusion regulation chamber.

A solid solution of both zirconia and yttria or calcia is typical as an oxygen ion conductive solid electrolyte to be used for the sensor element. Moreover, each solid solution of selium dioxide, thorium dioxide and hafnium dioxide, solid solution of perobuskeit type oxide and solid solution of trivalent metal oxide can also be used.

In addition, the porous electrode provided to both surfaces of the solid electrolyte can be formed by various methods, for example, sprayed metal coating by frame, chemical plating, vacuum evaporation using metals which have excellent heat resistivity such as Pt, Ru, Pd, Rh, Ir, Ag and Au, or sintering by printing of the paste of above metals.

The two sensor elements formed as explained above are respectively structured such that one porous electrode of each of the sensor elements faces the gas diffusion regulation chamber. The gas diffusion regulation chamber introduces the ambient measuring gas with regulation on the diffusion. This gas diffusion regulation chamber can be formed by arranging two sensor elements opposite to each other with an adequate interval therebetween, as the air-fuel ratio sensor explained for the prior art.

In addition, the gas diffusion regulation chamber can also be formed by placing a hollow spacer of alumina, spinel, forstelite, steatite and zirconia between two sensor elements and holes which connect the outside and gas diffusion regulation chamber are provided to a part of this spacer as the gas diffusion regulating section.

Next, the heater heats the two sensor elements to activate them up to the condition being ready to be used as the oxygen concentration cell element or oxygen pump element. For instance, the heater has a structure that a heat generating body is formed like a ribbon by the printing method on a surface of an inorganic insulation plate. As the inorganic insulation plate may be formed, for example, by alumina, spinel, forstelite, steatite or zirconia, etc. Meanwhile, the heat generating body may be formed, for example, by a heat resisting metal such as platinum, gold, etc.

In the apparatus for sensing air-fuel ratio of the present invention constituted as explained above, the means for outputting air-fuel ratio signal makes one of two sensor elements operate as the oxygen concentration cell element and the other sensor element as the oxygen pump element and outputs a signal of air-fuel ratio in accordance with the oxygen content in the exhaust gas.

The sensor element used as the oxygen concentration cell element is operated using the property indicated hereunder. Namely, since the oxygen ion moves in the solid electrolyte from the part of solid electrolyte surface with high partial pressure of oxygen gas to the part with low partial pressure when the oxygen ion conductive solid electrolyte is in an adequate temperature condition (for example, 400° C. or higher, when the solid electrolyte is formed by zirconia), a ratio of the partial pressures of oxygen gas between the electrodes can be detected as a voltage. In the case of the present invention, a voltage is generated between the electrodes at both surfaces of the oxygen concentration cell element in accordance with the ratio of the partial pressure of oxygen gas in the ambience (namely in the exhaust gas) to the partial pressure of oxygen gas in the gas diffusion regulation chamber, and this voltage is outputted by the means for outputting air-fuel ratio signal.

The sensor element used as the oxygen pump element is operated utilizing the property indicated hereunder. Since the oxygen ion moves in the solid electrolyte by applying a voltage to the oxygen ion conductive solid electrolyte, such movement can be sensed as an electric current value. For instance, when a voltage is applied with the electrode at a side of the gas diffusion regulation chamber used as the negative electrode by the means for outputting air-fuel ratio signal, the oxygen gas within the gas diffusion regulation chamber is pumped to the circumference, and when a voltage is applied with the electrode at that side used as the positive electrode, the oxygen gas in the circumference is pumped into the gas diffusion regulation chamber.

Accordingly, the means for outputting air-fuel signal may be constituted, as explained in the paragraph of prior art, so that a current flowing into the oxygen pump element is controlled in order to make the voltage generated at the electrodes of both sides of the oxygen concentration cell element constant. The air-fuel ratio can be detected from such controlled electric current value. Otherwise, the means for outputting air-fuel signal may be constituted so that a constant current is supplied to the oxygen pump element in 1 the direction of pumping the oxygen within the gas diffusion regulation chamber to the circumference. In this case, the air-fuel ratio can be detected from a voltage generated at the electrodes on both sides of the oxygen concentration cell element.

The present invention can also be applied to an air-fuel ratio sensor explained hereunder. That is a recently devised air-fuel ratio sensor which is provided with an atmospheric air introducing chamber in order to detect the air-fuel ratio in the entire region from rich to lean. The atmospheric air introducing chamber is formed at a side of the porous electrode which does not face the gas diffusion regulation chamber and the atmospheric air is introduced into the atmospheric air introducing chamber. In this case, however, the means for outputting air-fuel ratio signal may be formed to control a current flowing into the oxygen pump element in both directions and output such current value as the air-fuel ratio signal so that a voltage generated at the electrodes becomes constant, namely a partial pressure of oxygen gas in the gas diffusion regulation chamber becomes constant.

Next, the current-supply means supplies a current to the sensor element operated as the oxygen concentration cell element in such direction of pumping the ambient oxygen gas into the gas diffusion regulation chamber to operate the sensor element as not only an oxygen concentration cell element but also an oxygen pump element. This structure is adopted in order to assure that, as explained hereunder, the air-fuel ratio can be stably sensed from a voltage generated at the oxygen concentration cell element and a current flowing into the oxygen pump element even when a voltage to be applied to the heater changes.

Figure 5:
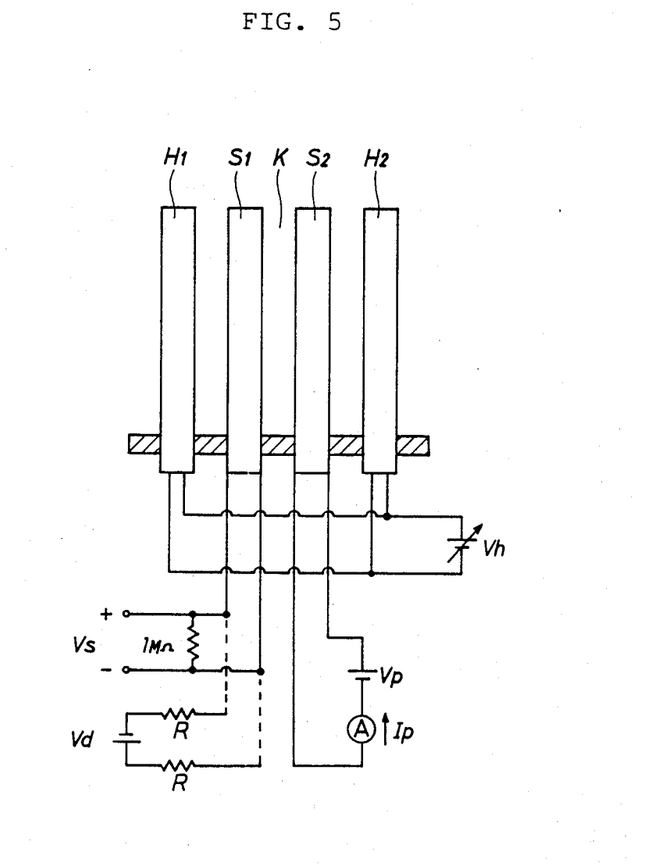
FIG. 5 is a circuit diagram indicating an experimental circuit used for explanation of the effect.
Figure 6:
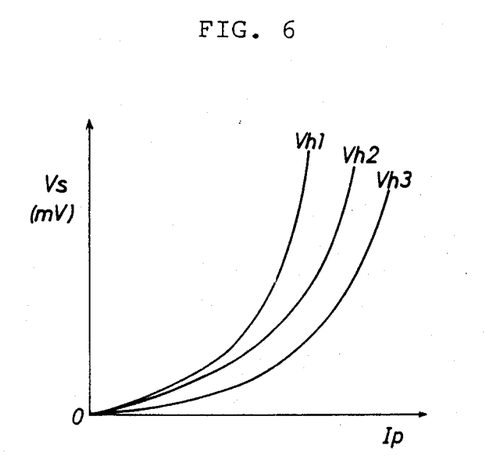
FIG. 6 is a characteristic diagram which indicates relationship between the voltage Vs generated at the oxygen concentration cell element and pump current Ip when a current is not applied to the oxygen concentration cell element.

The air-fuel ratio sensor is formed, for example, as shown in FIG. 5, by arranging two sensor elements S1 and S2, each of them formed like a plate, opposed to each other through an interval K as the gas diffusion regulation chamber and then providing the heaters H1 and H2 to both outsides of such sensor elements S1 and S2 in order to heat them. In case a voltage applied to the heater H1 and H2 (hereinafter, called a heater voltage) Vh is changed to Vh1, Vh2, Vh3 (where, Vh1<Vh2<Vh3), the relationship between the voltage Vs generated at the sensor element S1 as the oxygen concentration cell element and the current flowing into the sensor element S2 as the oxygen pump element (hereafter referred to as a pump current) Ip becomes as indicated in FIG. 6. Namely, when the pump current Ip=0, Vs becomes 0 and when the pump current Ip increases, the voltage Vs increases as sharply as the heater voltage Vh becomes lower.

This is because when the heater voltage Vh is low and the amount of heat generated by the heaters H1 and H2 becomes small, the temperature of the gas diffusion regulation chamber becomes low and transfer of oxygen to the gas diffusion regulation chamber is reduced. Namely, the amount of oxygen to be transferred is much reduced as the temperature becomes lower in the gas diffusion regulation chamber of the present invention in which gas diffusion is regulated by gas phase diffusion. Therefore, even when the pump current Ip of sensor element S2 is constant and a constant amount of oxygen in the interval K is brought to the outside, a lesser amount of oxygen is diffused into the interval K. This reduces the partial pressure of oxygen in the interval K and thereby an electromotive force Vs generated at the sensor element S1 becomes high.

Figure 7:
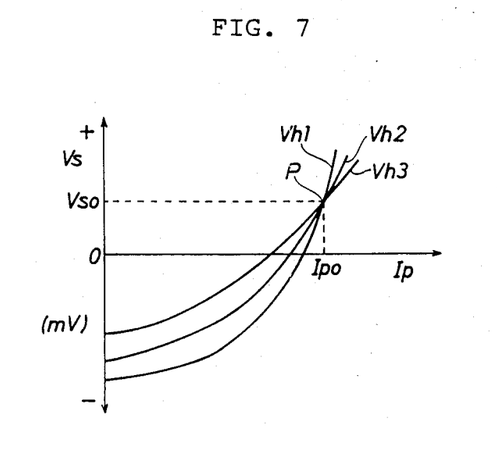
FIG. 7 is a characteristic diagram which indicates the relationship between the voltage Vs generated at the oxygen concentration cell element and the pump current Ip when a current is applied to the oxygen concentration cell element.

As indicated by a broken line in FIG. 5, a voltage Vd is applied to the sensor element S1 as the oxygen concentration cell element through a resistor R to allow a constant current to flow into the sensor element S1 in such a direction as supplying the ambient oxygen into the interval K. In this case, the relationship between the voltage Vs and pump current Ip becomes as follows. When pump current Ip=0, absolute value of the voltage Vs becomes larger as the heater voltage Vh is smaller as indicated in FIG. 7. The increase in voltage Vs becomes more sharp as the heater voltage Vh is smaller as indicated in FIG. 6. Therefore, when the pump current Ip is increased, the voltage Vs by each heater voltage Vh (Vh1, Vh2, Vh3) becomes close and converge at a specific voltage value Vso with a constant current Ipo, as shown in FIG. 7.

Namely, since the lower the temperature of sensor element S1, the larger the internal resistance r of the element S1, when a constant current Io is supplied to the sensor element S1 as explained above, the voltage Vs at Ip=0 changes (Vs=Io·r) depending on the heater voltage Vh. Therefore a specific point P is obtained where the voltage Vs can be fixedly determined from the pump current value Ip independent of the heater voltage Vh, due to the difference in the temperature characteristic (namely, gradient) of Vs—Ip shown in FIG. 6.

Therefore, when a current flows in such a direction of pumping the ambient oxygen into the gas diffusion regulation chamber by applying a specified voltage to the oxygen concentration cell element by the means for current supply, the stable voltage Vs can be obtained even when the heater voltage Vh changes. So, the air-fuel ratio can be sensed with high accuracy even when the heater voltage Vh changes by forming the means for outputting air-fuel ratio signal in such a way as follows. The pump current Ip flowing into the oxygen pump element is controlled so that a voltage generated on the oxygen concentration cell element becomes Vso. In this case, the air-fuel ratio is sensed from such current value Ip. Alternatively, the pump current Ipo is caused to flow into the oxygen pump element and in this case the air-fuel ratio is sensed from the voltage Vs generated at the oxygen concentration cell element.

Supply current to the oxygen concentration cell element can be realized by using a constant current source or setting a voltage Vd as a constant voltage and then setting a resistance value of resistor R to such a large value that the current is not influenced by the internal resistance of the cell element. Thereby, the point where Vs and Ip are most stabilized theoretically can be obtained. In this case, however, since Vs and Ip do not always cross on a point because a resistance value of electrodes, etc., also changes due to temperature change resulting from change in heater voltage Vh, it is desirable to change a current value or a voltage applied from the current source depending on the heater voltage Vh. However, since such structure requires a constant current circuit, a constant voltage circuit or a control circuit which controls a current or voltage in accordance with the heater voltage Vh, the circuit may be simplified for practical use by directly applying the heater voltage Vh to the oxygen concentration cell element through the resistor R.

In such an apparatus for sensing air-fuel ratio of the prior art, the sensing result of air-fuel ratio changes depending on the change in ambient pressure. But such change can be suppressed by employing such structure as explained above, because the change in detection result responding to change in atmospheric pressure depends on the fact that the amount of oxygen transferred to the gas diffusion regulation chamber changes due to the change in atmospheric pressure (when the atmospheric pressure becomes lower, the amount of oxygen transferred to the gas diffusion regulation chamber becomes smaller and the internal resistance r of the element S1 becomes larger because the amount of oxygen surrounding S1 becomes small).

As explained previously, in the apparatus for sensing air-fuel ratio of the present invention, the sensor element which has been operated as the oxygen concentration cell element is also operated as the oxygen pump element. When the pump current Ip flowing into the oxygen pump element is 0, the voltage Vs generated at the oxygen concentration cell element can be changed in accordance with the voltage Vd applied to the oxygen concentration cell element. Therefore, a constant pump current Ipo and a particular voltage Vso can be obtained independent of the heater voltage Vh. Thereby, the stabilized air-fuel ratio signal can always be obtained even when the heater voltage Vh has changed, by forming the means for outputting the air-fuel ratio signal in such a way that the pump current flowing into the oxygen pump element is controlled so that a voltage generated at the oxygen concentration cell element becomes Vso and the air-fuel ratio is sensed from such current value, or that in case a constant pump current Ipo is caused to flow into the oxygen pump element, the air-fuel ratio is sensed from a voltage generated at the oxygen concentration cell element. Moreover, in this case, change in ambient pressure can be compensated.

BRIEF DESCRIPTION OF THE DRAWINGS

FIGS. 2 to 4 show the structures of an air-fuel ratio sensor 1; where

FIGS. 5 to 7 respectively show the effect of the present invention; where

DETAILED DESCRIPTION OF THE PREFERRED EMBODIMENTS

The preferred embodiments of the present invention will be explained with reference to the accompanying drawings. The present invention is not limited only to the embodiment explained hereunder and also allows various modifications without departure from the scope thereof. The figures attached are different in the scale for the convenience of explanation.

Figure 1:
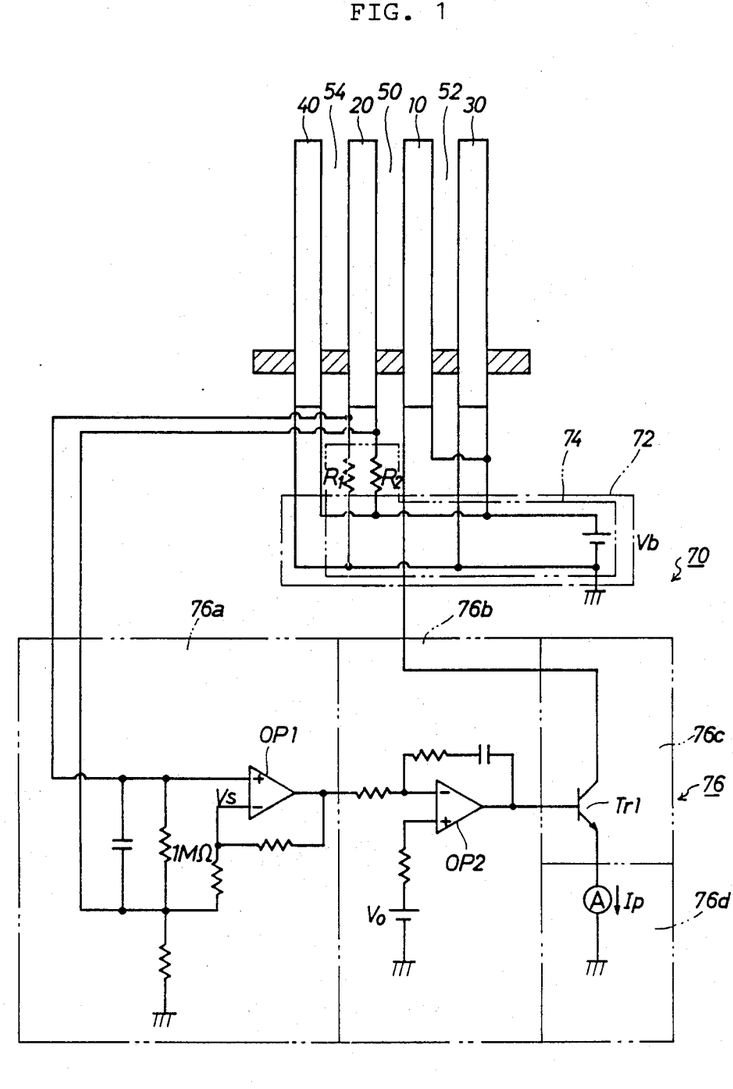
FIG. 1 is an outline of overall structure of an apparatus for sensing air-fuel ratio as an embodiment.

FIG. 1 is outline of the structure of the entire part of an apparatus for sensing air-fuel ratio as the embodiment of the present invention.

Figure 2:
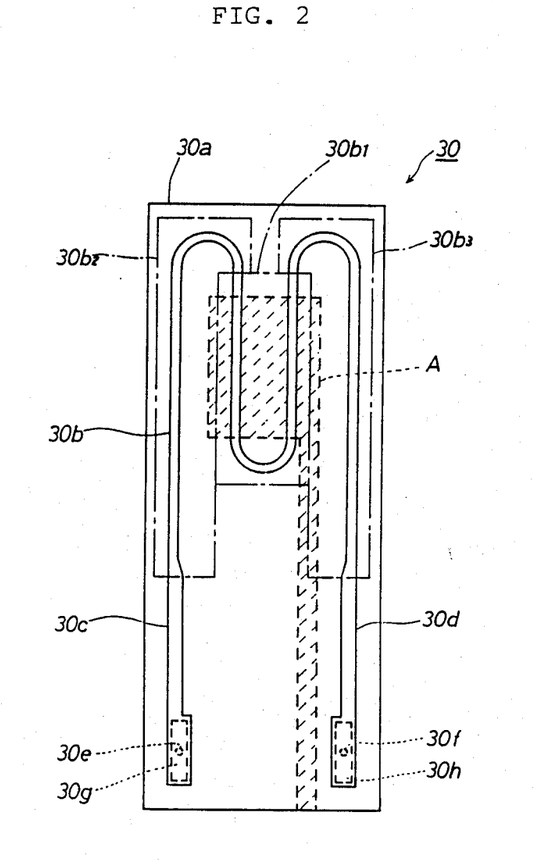
FIG. 2 is a plan view.
Figure 3:
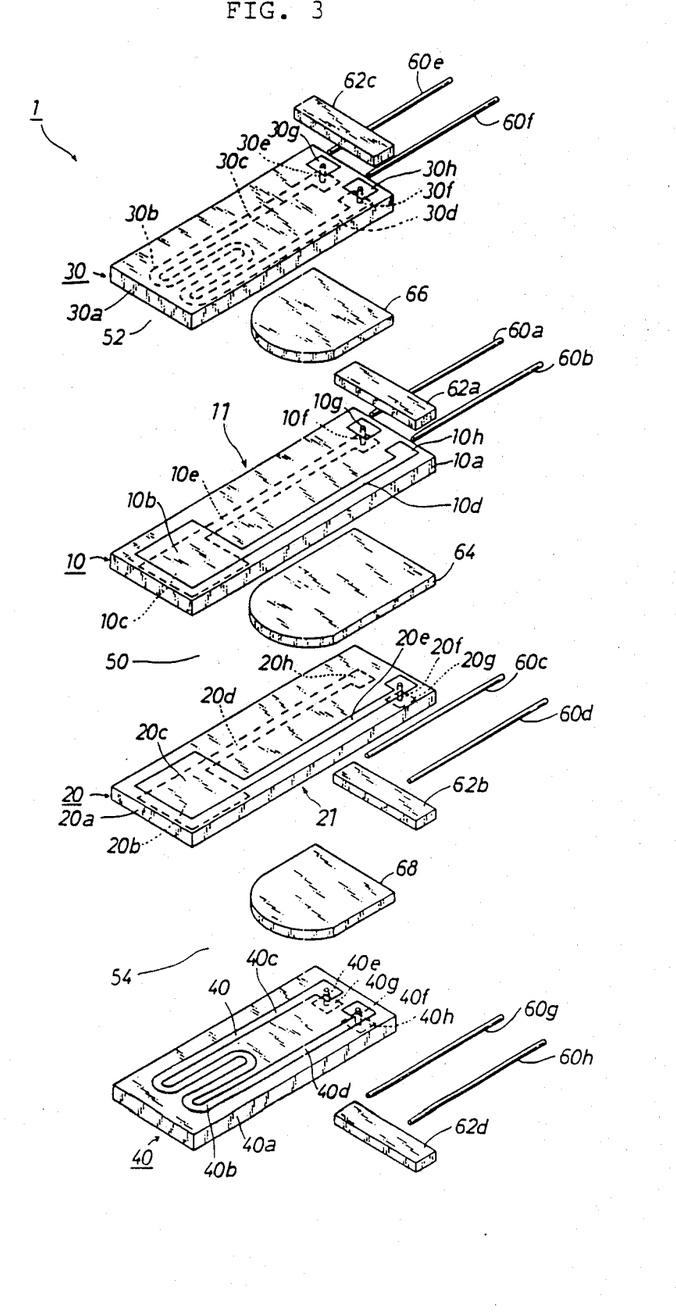
FIG. 3 is a disassembled perspective view and FIG. 4 is a side elevation.
Figure 4:
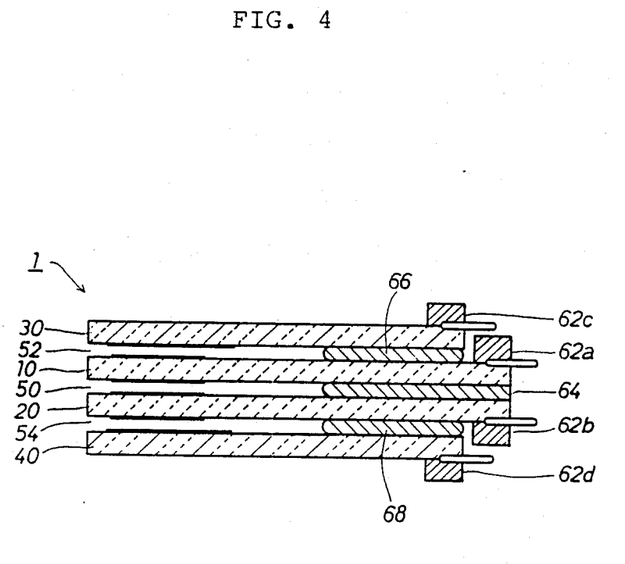

FIGS. 2 to 4 show the structure of air-fuel ratio sensor used in the embodiment of the present invention. FIG. 2 is a plan view. FIG. 3 is a disassembled perspective view and FIG. 4 is a sectional view.

As indicated in FIG. 3 and FIG. 4, the air-fuel ratio sensor 1 is formed by a sensor element (hereinafter referred to as oxygen pump element) 10 which is operated by a sensing circuit explained later as the oxygen pump element and is formed like a plate using the oxygen ion conductive solid electrolyte, a sensor element (hereinafter referred to as oxygen concentration cell element) 20 which is operated by the sensing circuit explained later as the oxygen concentration cell element and is formed like a plate using the oxygen ion conductive solid electrolyte, and two heaters 30 and 40 formed like a plate. The oxygen pump element 10 and the oxygen concentration cell element 20 are arranged opposite to each other through a gap 50. In the case of this embodiment, the gas diffusion regulation chamber is formed by this gap 50. Two heaters 30 and 40 are arranged through the gaps 52 and 54 in the side opposed to the side facing to the oxygen pump element 10 and oxygen concentration cell element 20.

The oxygen pump element 10 and oxygen concentration cell element 20 are mainly formed by the sintered plates of oxygen ion conductive solid electrolyte 11, 21 in the thickness of 0.7 mm, width of 4 mm and length of 35 mm. At the end portions of the sensor elements 10 and 20, the square-shaped electrodes 10b, 10c or 20b, 20c consisting of the heat-resisting metal layer are provided in the position opposed to the front and rear surfaces of the sensor elements and is also a little drawn inside from three edge portions. The lead lines 10d, 20d consisting of the heat-resisting metal layer provided like the belts extending in straight to the side of the root portion of the plates 10a, 20a from one of two angled portions in the direction toward the root portion of the one square-shaped electrodes 10b, 20b. In the same way, the lead lines 10e, 20e are provided like the belts extending in straight to the side of root portion of the plates 10a, 20a from the angled portion opposed to the electrodes 10c, 20c among two angled portions in the direction toward the root portion of the other square-shaped electrodes 10c, 20c. The lead lines 10e and 20e are electrically connected to the terminal portions 10g, 20g at the opposed surface through the through-holes 10f, 20f provided through the front and rear surfaces of plate 10a, 20a at the root portions. The lead lines 10d and 20d form the terminal portions 10h, 20h respectively at the root portions. As a result, the terminal portions 10g and 10h, 20g and 20h of the two electrodes 10b and 10c, 20b and 20c are arranged in the same surface.

The heaters 30 and 40 are then explained hereunder. The heaters 30 and 40 are mainly formed by the electrically insulated sintered plates 30a, 40a with thickness of 0.8 mm, width of 4 mm and length of 30 mm. At the end portions of the one surface of the heaters 30 and 40, the heat-generating resistors 30b, 40b consisting of the heat-resisting metal layer are provided like waves. Moreover, the lead lines 30c and 30d, 40c and 40d consisting of heat-resisting metal layer are formed like the belts extending in straight toward the root portions of plates 30a, 40a from the both end portions of the heat-generating resistors 30b and 40b. The lead lines 30c and 30d, 40c and 40d are respectively connected electrically to the terminal portions 30g and 30h, 40g and 40h at the opposed surface through the through-holes 30e and 30f, 40e and 40f provided through the front and rear surfaces of the plates 30a and 40a at the root portion thereof.

The heat-generating resistor 30b is formed by a first heating portion 30b1 and two second heating portions 30b2, 30b3 as shown in FIG. 2.

The first heating portion 30b1 has the width of 0.30 mm, while the second heating portions 30b2 and 30b3 have the width of 0.35 mm and the lead lines 30c, 30d have the width of 1.20 mm. Resistance per unit length is larger as the width of pattern is narrower and more heat is generated when resistance per unit length is higher. Therefore, when the electrical power is supplied to the heat-generating resistor 30b, temperature of electrode 10b (the corresponding position A is indicated by a broken line in FIG. 2) of the oxygen pump element heated by the narrowest first heating portion 30b1 becomes higher and temperature at periphery of gap 50 heated by the second heating portions 30b2, 30b3 which are wider than the first heating portion becomes comparatively low.

Although not illustrated in the figure, the heat-generating resistor 40b is also formed in the same way as the heat-generating resistor 30b.

The terminal portions 10g, 10h, 20g, 20h, 30g, 30h, 40g, 40h of the oxygen pump element 10, the oxygen concentration cell element 20 and the heaters 30 and 40 are connected with the platinum leads 60a to 60h as the lead wires. The end portion sides of platinum leads 60a to 60h are covered with the insulators 62a to 62d in the thickness of 0.8 mm, length of 4 mm and width of 4 mm. The gap 50 between the oxygen pump element 10 and oxygen concentration cell element 20 is formed by a spacer 64 in the thickness of 100 micron and the gaps 52, 54 between the oxygen pump element 1 and the heater 30 or between the oxygen concentration cell element 20 and the heater 40 are formed by spacers 66, 68 in the thickness of 80 micron.

The air-fuel ratio sensor 1 of the present embodiment is manufactured as explained hereunder.

First, the oxygen pump element 10 and oxygen concentration cell element 20 are manufactured in the processes (1)-1 to (1)-10 as explained below and the gap 50 as the gas diffusion regulation chamber is formed by attaching these elements 10, 20 through the heat resisting cement.

(1)-1 $ZrO_2$ (94 mol %) and $Y_2O_3$ (6 mol %) are mixed and milled for 40 hours in the wet processing system.

(1)-2 This milled mixture is dried and temporarily baked for 2 hours at 1300° C.

(1)-3 This baked material is milled again for 40 hours in the wet processing system and thereby the raw material powder of solid electrolyte is obtained.

(1)-4 An organic binder, methyl-ethyl-keton, toluene, etc. are added to the raw material powder of solid electrolyte in order to obtain slurry.

(1)-5 A sheet material of 0.9 mm thick is obtained by the doctor blade method from this slurry.

(1)-6 The paste for electrode is obtained by adding solid electrolyte raw material powder in 10 wt % obtained in the step (1)-3, solvent and binder to the mixture mixing the platinum black and platinum sponge in the ratio of 2:1.

(1)-7 The patterns of electrode, lead line and terminal portion as indicated in FIG. 2 are formed in the thickness of 40 micron on the sheet material obtained in the step (1)-5 by screen printing of the paste for electrode obtained in the step (1)-6.

(1)-8 After the sheet material on which the paste for electrode is printed is cut into the shape of each element, the end portion of platinum wire with 0.3 mm$\phi$ is placed on the pattern of terminal portion formed on the sheet material of each element and moreover a single sheet of sheet material obtained in the step (1)-5 is placed thereon and these are layered by the press.

(1)-9 After the sheet material of each element is processed for 6 hours at 300° C. for eliminating resin content, it is then baked under the atmospheric condition for 4 hours at 1500° C. Thus, the oxygen pump element 10 and oxygen concentration cell element 20 are formed.

(1)-10 The elements 10 and 20 are fixed with heat resisting cement so that the gap between the electrodes 10c and 20c provided opposite to the elements 10, 20 manufactured as explained above becomes 100 micron. This heat resisting cement used for fixing works as the spacer 64. The gap 50 formed by such heat resisting cement becomes a gas diffusion regulation chamber.

Next, the heaters 30, 40 are manufactured respectively in the steps (2)-1 to (2)-4 explained hereunder and these are attached to the structure assembled in the step (1)-10.

(2)-1 A sheet material of 0.9 mm thick is formed in the same ways as steps (1)-4 and (1)-5 from the raw material powder consisting of $Al_2O_3$ of 92 wt %, MgO of 3 wt %, $SiO_2$ of 3 wt %, CaO and so on.

(2)-2 Like the step (1)-7, the patterns of heat-generating resistor, lead line and terminal portion as indicated in FIG. 2 are formed on the sheet material formed in the step (2)-1 in the thickness of 25 micron and width as explained above by the screen printing using the paste for electrode formed in the step (1)-6.

(2)-3 Like the steps (1)-8 and (1)-9, after the sheet material printed the paste for electrode as explained above is cut into the shape of heating element, the end portion of platinum line with 0.3 mm$\phi$ is placed on the pattern of terminal portion on the sheet material of the heating element and a single sheet of the sheet material obtained in the step (1)-5 is placed thereon and these are layered by the press. After the sheet material of heating element is processed for 6 hours at 300° C. for eliminating resin content, it is baked under the atmospheric condition for 2 hours at 1520° C. to obtain the heaters 30 and 40 having the heating generating resistor of 2.5 ohms.

(2)-4 The heaters 30 and 40 obtained in the step (2)-3 are attached to the structure obtained in the step (1)-10 using the heat resisting cement so that the gap to the structure becomes 80 micron. The heat resisting cement used for attachment becomes the spacers 66, 68 explained above.

As shown in FIG. 1, the air-fuel ratio sensor formed as explained previously is connected to the sensing circuit 70, which comprises a heater voltage supply system 72 as the voltage applying means which supplies a battery voltage Vb to the heaters 30 and 40 to heat respectively the oxygen pump element 10 and the oxygen concentration cell element 20, a current supply system 74 as the current supply means which applies a battery voltage Vb to the oxygen concentration cell element 20 through the resistor R1 (=10k ohms) and resistor R2 (=30k ohms) in such a direction as pumping the ambient oxygen gas into the gap 50 as the gas diffusion regulation chamber, and an air-fuel ratio signal output circuit 76 as the means for outputting air-fuel ratio signal which outputs the air-fuel ratio signal in accordance with oxygen concentration in the atmospheric condition on the basis of the voltage Vs generated at the oxygen concentration cell element 20 and a pump current Ip flowing into the oxygen pump element 10.

The air-fuel signal output circuit 76 has the structure to control the pump current Ip flowing into the oxygen pump element 10 so that the voltage generated at the oxygen concentration cell element 20 becomes preset target value Vo (15 mV in this embodiment) and senses the air-fuel ratio from such current value Ip.

Namely, the air-fuel ratio signal output circuit 76 comprises a voltage sensing circuit 76a formed by an operational amplifier OP1 which senses the voltage generated at the electrodes on both sides of the oxygen concentration cell element 20, a comparison/integral circuit 76b formed by an operational amplifier OP2 which compares a sensing voltage Vs output from the voltage sensing circuit 76a with a preset target value Vo and outputs a control voltage which is gradually lowered in the rate of specified integral constant when the sensed voltage Vs is larger than the target value Vo or is gradually increased in the rate of specified integral constant when Vs is smaller than Vo, a pump current control circuit 76c formed by a transistor Tr1 which controls the pump current Ip flowing into the oxygen pump element 10 in accordance with the control voltage output from the comparison/integral circuit 76b and a pump current sensing circuit 76d which senses the pump current Ip controlled by the pump current control circuit 76c as the air-fuel ratio signal.

The target value Vo is a value of voltage Vso at the cross point P of the sensing result as shown in FIG. 7 obtained by applying the battery voltage Vb to the oxygen concentration cell element 20 through the resistors R1 and R2, as explained above, changing the battery voltage Vb, and obtaining the relationship, by experiment, between the pump current Ip flowing into the oxygen pump element 10 in every voltage and the voltage Vs generated at the oxygen concentration cell element 20.

Next, temperature change in air-fuel ratio signal is explained as below.

Change in pump current Ip when the voltage Vb applied to the heater changes 10V, 9.5V, 9V, namely temperature change in air-fuel ratio signal due to change in voltage Vb applied to the heater (namely a battery voltage) is obtained by experiment. For comparison, the resistance value of resistor R2 in FIG. 1 is set to an infinitive value and the apparatus for sensing air-fuel ratio not providing the current supply system 74 for the oxygen concentration cell element 20 is formed, and thereby temperature change in the air-fuel ratio signal has also be obtained experimentally. The experimental results are shown in Table 1 and Table 2.

TABLE 1

| Voltage applied to heater | Vs mV (Ip = 0) | Ip mA (Vo = 15) | Ip mA (Vo = 25) |
|---|---|---|---|
| 10 V | −11.5 | 79.5 | 89.5 |
| 9.5 V | −13.0 | 79.0 | 88.5 |
| 9.0 V | −15.0 | 78.0 | 87.0 |

TABLE 2

| Voltage applied to heater | Vs mV (Ip = 0) | Ip mV (Vo = 40) |
|---|---|---|
| 10 V | −0.2 | 93.5 |
| 9.5 V | −0.1 | 90.0 |
| 9.0 V | −0.1 | 86.0 |

In above tables 1 and 2, Vs is a voltage value generated at the oxygen concentration cell element 20 when the pump current Ip=0 and Ip is a pump current value obtained when the voltage Vs generated at the oxygen concentration cell element 20 is controlled so that it becomes a value indicated in the parentheses.

The experimental results shown in Table 1 suggest that when the oxygen concentration cell element 20 is operated also as the oxygen pump element by allowing a current to flow in such direction as pumping the ambient gas into the gas diffusion regulation chamber 50 by applying a battery voltage Vb to the oxygen concentration cell element 20 as in the case of the present embodiment, change in pump current Ip (namely, air-fuel ratio sensing signal) for change in voltage applied to the heater (battery voltage Vb) can be suppressed more effectively and the air-fuel ratio can be sensed with higher accuracy in comparison to that (Table 2) in case the oxygen concentration cell element 20 is operated only as it is like the prior art.

Next, Table 3 shows the experimental results obtained for change in pump current Ip, namely pressure change in air-fuel ratio signal in such a case that the atmospheric pressure is changed using an apparatus for sensing air-fuel ratio of the present embodiment and the apparatus for sensing air-fuel ratio used for comparison explained above. Where, voltage applied to the heater is set to a constant value of 9.5V.

TABLE 3

| Apparatus Pressure mmHG | Embodiment | | Comparison |
| --- | --- | --- | --- |
| | Ip mA (Vo = 15) | Ip mA (Vo = 25) | Ip mA (Vo = 40) |
| 200 | 78.2 | 87.5 | 87.2 |
| 760 | 79.0 | 88.5 | 90.0 |

From the above experimental results in Table 3, it is apparent that change in pump current Ip can be suppressed for a pressure change in atmospheric condition and accuracy of sensing air-fuel ratio can be improved in case a current is allowed to flow into the oxygen concentration cell element 20 because, as is already explained, change of sensing air-fuel ratio by pressure change results from change in oxygen amount introduced from the gas diffusion regulation chamber due to the pressure change like the change in voltage applied to the heater. Namely, when ambient pressure becomes low, the exhaust gas is not introduced easily into the gas diffusion regulation chamber. As a result, a partial pressure of oxygen in the gas diffusion regulation chamber is lowered and the amount of oxygen is also reduced and thereby an internal resistance of oxygen concentration cell element becomes slightly larger. However, in case the apparatus for sensing air-fuel ratio is formed like the present embodiment, change in air-fuel ratio signal due to the change in amount of oxygen supplied to the gas diffusion regulation chamber is suppressed by the compensated value (Ior) obtained from the internal resistance of element and thereby change in air-fuel ratio signal for pressure change can also be suppressed.

What is claimed is:

1. An apparatus for sensing air-fuel ratio comprising:
 (a) an air-fuel ratio sensor for sensing oxygen concentration in an exhaust gas, said air-fuel ratio sensor including (a1) two sensor elements each of which is formed by coating a pair of porous electrodes on both surfaces of an oxygen ion conductive solid electrolyte plate, (a2) a gas-diffusion regulation chamber which faces one of the porous electrodes of one element and one of the porous electrodes of the other element and restricts diffusion of the exhaust gas by molecular diffusion and (a3) a heater which heats said two sensor elements;
 (b) voltage-applying means for applying voltage to said heater in order to heat said two sensor elements;
 (c) means for outputting an air-fuel ratio signal responsive to the oxygen concentration in the exhaust gas by making one of said two sensor elements operate as an oxygen concentration cell element whose reference electrode is in contact with a controlled atmosphere and the other of said two sensor elements operate as an oxygen pump element, means for detecting a pumping current controlled by an output of said oxygen concentration cell element, said air-fuel ratio being detected from an amount of electric current supplied to said oxygen pump element to control a voltage developing between said porous electrodes of said oxygen concentration cell element at a target value which is determined at such value that is invariable to change in voltage applied to said heater; and
 (d) a resistor with higher resistance value than that of said oxygen concentration cell element;
 (e) current-supply means for supplying an electric current to said oxygen concentration cell element by applying constant preset voltage to said oxygen concentration cell element through said resistor, said electric current having such a direction as to transport oxygen gas from ambient exhaust gas to said gas diffusion regulation chamber.

2. The apparatus for sensing air-fuel ratio according to claim 1, wherein said solid electrolyte plate is made from solid solution of zirconia and yttria.

3. The apparatus for sensing air-fuel ratio according to claim 1, wherein said gas-diffusion regulation chamber is a space formed by laminating said two sensor elements with a heat-resistant cement therebetween.

4. The apparatus for sensing air-fuel ratio according to claim 1, wherein said porous electrodes are formed by sintering heat-resistant metal paste printed on said solid electrolyte plate.

5. The apparatus for sensing air-fuel ratio according to claim 1, wherein the heater is a ribbon-shaped heater which is printed on an insulating inorganic body facing each of said two sensor elements, and comprises a narrow first heating member facing a portion of the sensor element and a wide second heating member facing another portion of the sensor element.

6. The apparatus for sensing air-fuel ratio according to claim 1, wherein the restriction of the diffusion is accomplished by a gap.

* * * * *